(12) United States Patent
Dobbs (10) Patent No.: US 8,759,780 B2
(45) Date of Patent: Jun. 24, 2014

(54) PIPELINE INSPECTION

(75) Inventor: John M. Dobbs, Beverly, MA (US)

(73) Assignee: Analogic Corporation, Peabody, MA (US)

(*) Notice: Subject to any disclaimer, the term of this patent is extended or adjusted under 35 U.S.C. 154(b) by 0 days.

(21) Appl. No.: 13/119,791

(22) PCT Filed: Mar. 13, 2009

(86) PCT No.: PCT/US2009/037085
§ 371 (c)(1),
(2), (4) Date: Mar. 18, 2011

(87) PCT Pub. No.: WO2010/033265
PCT Pub. Date: Mar. 25, 2010

(65) Prior Publication Data
US 2011/0168900 A1    Jul. 14, 2011

Related U.S. Application Data

(60) Provisional application No. 61/192,573, filed on Sep. 19, 2008.

(51) Int. Cl.
*G01N 23/18* (2006.01)
*G01N 23/00* (2006.01)
*G01N 23/02* (2006.01)

(52) U.S. Cl.
CPC ............... *G01N 23/00* (2013.01); *G01N 23/02* (2013.01); *G01N 23/18* (2013.01)
USPC ..................................................... 250/360.1

(58) Field of Classification Search
CPC ....... G01N 23/00; G01N 23/02; G01N 23/18; G01N 2223/628
USPC ........................................................ 250/358.1
See application file for complete search history.

(56) References Cited

U.S. PATENT DOCUMENTS 4,974,246 A    11/1990  Heiskel
5,698,854 A    12/1997  Gupta (Continued)

FOREIGN PATENT DOCUMENTS

DE    69330089    9/2001
EP    0310874    4/1989

(Continued)

OTHER PUBLICATIONS

Jan O. Hallset: "A Vision system for an autonomous underwater vehicle" 11th IAPR International Conference on Pattern Recognition,1992, pp. 320-323, XP002573262 Retrieved from the Internet: URL:http://ieeexplore.ieee.org/stamp/stamp.jsp?tp= &arnumber=201566>.

(Continued)

*Primary Examiner* — Marcus Taningco
(74) *Attorney, Agent, or Firm* — Cooper Legal Group LLC (57) ABSTRACT

The present application provides techniques and/or systems for inspecting a pipe, or rather measuring one or more characteristics of a pipe, using radiation. A carriage, mounted to the pipe, may provide a mechanism for propelling a radiation source and a detector along the pipe. The detector is configured such that it can receive radiation that has traversed both a wall of the pipe and an obstacle, such as a pipe support. In this way, portions of a pipe that are traditionally difficult to inspect may be inspected easily with minimal human intervention.

20 Claims, 6 Drawing Sheets

(56) References Cited

U.S. PATENT DOCUMENTS

| | | | |
|---|---|---|---|
| 5,963,030 A * | 10/1999 | Stark | 324/229 |
| 6,925,145 B2 | 8/2005 | Batzinger et al. | |
| 7,594,448 B2 * | 9/2009 | Jacobson et al. | 73/865.8 |
| 8,024,066 B2 | 9/2011 | Reverte et al. | |
| 2005/0041775 A1 * | 2/2005 | Batzinger et al. | 378/59 |
| 2006/0078091 A1 * | 4/2006 | Lasiuk et al. | 378/198 |
| 2006/0253228 A1 | 11/2006 | Abraham et al. | |
| 2008/0267345 A1 * | 10/2008 | Nagumo et al. | 378/11 |
| 2009/0232282 A1 * | 9/2009 | Belson et al. | 378/203 |

FOREIGN PATENT DOCUMENTS

| | | |
|---|---|---|
| EP | 1245949 | 10/2002 |
| GB | 2203535 | 10/1988 |
| GB | 2394549 | 4/2004 |
| WO | 9733212 | 9/1997 |

OTHER PUBLICATIONS

Anonymous: "Pipeline monitoring system" GPS World, Dec. 1, 2004, XP002573263 Retrieved from the Internet: URL:http://findarticles.com/p/articles/mi_mOBPW/is_12_15/ai_n8694232/>.

International Search Report cited in related application No. PCT/US2009/047146 dated Apr. 9, 2010.

International Search Report cited in related application No. PCT/US2009/037085 dated Jul. 15, 2009.

Walker, Stan M., "US13 New NDE developments support rapid, economical screening for flow-accelerated corrosion", First International Conference on NDE in Relation to Structural Integrity for Nuclear and Pressurised Components, NDT.net Oct. 1999, vol. 4 No. 10.

Canadian Office Action cited in Canadian Application No. 2,737,555 dated Oct. 24, 2012, 3 pgs.

Preliminary Amendment cited in U.S. Appl. No. 13/119,794 dated Mar. 18, 2011, 11 pgs.

Int. Preliminary Report in PCT Application No. PCT/US2009/037085 dated Mar. 22, 2011, 8 pgs.

Canadian Office Action in Canadian Application No. 2,737,603 dated Jul. 2, 3013, 3 pgs.

Reply Canadian Office Action in Canadian Application No. 2,737,555 dated Mar. 18, 2013, 20 pgs.

Restriction/Election Office Action in U.S. Appl. No. 13/119,794 dated Oct. 10, 2013, 8 pgs.

Reply Restriction/Election Office Action in U.S. Appl. No. 13/119,794 dated Nov. 12, 2013, 9 pgs.

Non-Final Office Action in U.S. Appl. No. 13/119,794 dated Dec. 19, 2013, 10 pgs.

Canadian Office Action in Canadian Application No. 2,737.555 dated Dec. 18, 2013, 2 pgs.

* cited by examiner

PIPELINE INSPECTION

CROSS REFERENCE TO RELATED APPLICATIONS

This application claims the benefit of U.S. provisional application Ser. No. 61/192,573 filed Sep. 19, 2008, which is incorporated herein by reference in its entirety.

BACKGROUND

The present application relates to the examination of pipelines or other fluid transport vessels (e.g., pipeline section, column, heat exchanger silo, etc.) using radiation. It finds particular application to the use of ionizing radiation in aboveground oil pipeline inspections. It also relates to other applications where data from a movable scanner may be used to provide information about the structure and/or dynamics of an object being scanned.

Radiation, in general, penetrates an object under examination. The object is exposed to radiation, and information is acquired based upon the radiation absorbed by the object, or rather an amount of radiation that is able to pass through the object. Typically, highly dense objects absorb more radiation than less dense objects. For example, a thick metal plate may absorb more radiation than a thin metal plate, and thus information related to various properties of the plates (e.g., thickness, composition, etc.) may be acquired based upon the radiation that is absorbed.

Radiation devices commonly comprise a radiation source and a detector array. The radiation source and detector array are typically positioned on substantially diametrically opposing sides of the object under examination. Radiation, emitted from the radiation source, interacts with the object under examination. Radiation that traverses the object is detected by the detector array. Data, produced based upon the detected radiation, may then be used to determine characteristics of the object under examination and/or used to produce an image of the object.

Inspection of pipelines is common to detect defects, obstructions, and other flaws in the manufacturing process that may affect the flow of a fluid. Additionally, over time pipelines may endure abrasion, corrosion, etc. that may lead to structural fatigue, divots, or cracks that cause the pipeline to leak or otherwise affect performance. Leakage of a fluid may lead to substantial monetary cost and production delays for the entity responsible for the pipeline, so the sooner defects, cracks, wall thinning, etc. can be detected, the better.

Radiation is utilized in the inspection process to measure characteristics of a pipeline that are unable to be visually inspected. For example, radiation provides a mechanism for measuring the thickness of a pipeline's wall. While other mechanisms for measuring similar characteristics have been devised, radiation works particularly well for some applications because results are minimally affected by properties of the pipeline that are not being measured, such as an insulation layer covering an external surface of the pipeline's wall, for example. Additionally, unlike some other mechanisms that measure characteristics from within the pipeline (e.g., a "pig"), radiation devices may measure the characteristics from locations external to the pipeline.

One type of radiation inspection device used to inspect pipelines is disclosed in U.S. Pat. No. 5,698,854 to Gupta. Gupta describes a carriage configured to be moveably mounted to a pipeline and to circumferentially enclose a scanning portion of the pipeline. As the carriage slowly moves axially along a portion of the pipeline, a radiation source emits radiation that may be detected by a detector array.

Another type of radiation inspection device used to inspect pipelines is disclosed in U.S. Pat. No. 6,925,145 to Batzinger et al. Batzinger et al. describe a controller that causes a scanner to move along a pipeline. In one embodiment, a radiation source and a detector array that are part of the scanner are connected to an arcuate bracket that allows the radiation source and detector array to be rotated while moving along the pipeline. However, the Batzinger et al. device is deficient at least in that it does not allow the scanner to inspect a portion of the pipeline adjacent to, or rather touching, a pipe support.

While current radiation devices have proven useful in some inspection applications, there remains room for improvement. Obstructions (e.g., beams, marking posts), directional changes in the pipeline, etc. prevent current radiation inspection devices from collecting data related to portions of the pipeline that are in close proximity to the obstruction, such as portions touching and/or nearby the obstruction. Obstructions also make it difficult and/or impossible for some radiation inspection devices to travel past the obstruction and continue scanning without the device being disconnected from the pipe and then reassembled on the other side of the obstruction. Some radiation inspection devices are also not configured to rotate in a transverse, or rather radial, direction with respect to the pipeline, making it more difficult to acquire accurate and/or reliable data for various portions of the pipeline. Additionally, some of the radiation inspection devices require significant human intervention (e.g., piloting the device as it moves axially along the pipeline) which may make operation of a device very costly. The slow speed at which some radiation inspection devices move axially along a pipeline also poses a problem in some applications because it takes too long to scan a meaningful length (e.g., thousands of miles) of the pipeline.

SUMMARY

Aspects of the present application address the above matters, and others. According to one aspect, a pipe inspection apparatus is provided. The apparatus comprises a carriage configured for movement along a stationary pipe and an ionizing radiation source. The apparatus also comprises a radiation detector carried by the carriage. The detector detects radiation from the source, which radiation has traversed a pipe support and a wall of the pipe.

According to another aspect, a method is provided. The method comprises using a scanning apparatus that travels along a pipeline to detect ionizing radiation that has traversed a wall of the pipeline and an obstacle that substantially impedes the motion of the scanning apparatus along the pipeline. The method also comprises using the detected radiation to generate information indicative of a characteristic of the pipeline.

According to yet another aspect, an apparatus for scanning a pipe supported by first and second axially-spaced transverse supports is provided. The apparatus comprises a scanner configured to scan the pipe at the first and second supports and therebetween. The apparatus also comprises a carriage configured to mount to an exterior of the pipe and to carry the scanner between the first and second supports.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
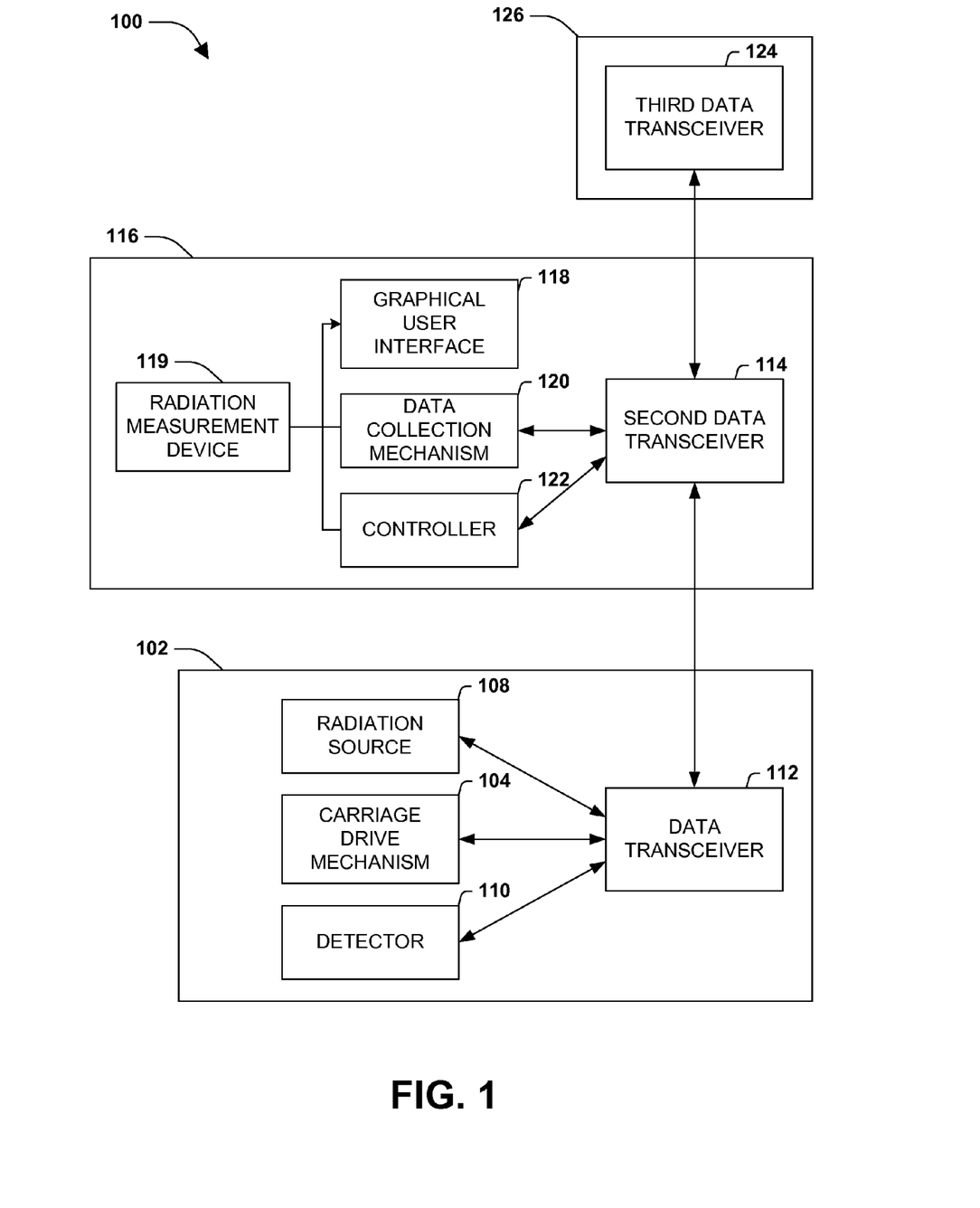
FIG. 1 is a schematic block diagram illustrating an example apparatus for inspecting a pipe.

FIG. 1 is a system block diagram illustrating an example apparatus 100 for generating information indicative of one or more characteristics (e.g., wall thickness, positions of pits or divots, etc.) of a stationary pipe, or rather a pipeline, based upon radiation that has traversed the pipe. While the apparatus 100 may be used with pipes of various dimensions, the apparatus 100 finds particular application with hydrocarbon, or rather oil pipes. These pipes are typically about five to eight inches in diameter, comprise two to three inches of foam insulation, are covered with twenty to twenty-four gauge steel wrapping, and have a wall thickness between 0.250 and 0.500 inches.

The example apparatus 100 comprises a carriage 102 (e.g., a data taking head) configured for movement along the stationary pipe. The carriage 102 may be physically attached to the pipe (e.g., on tracks) and/or may be rested on the pipe (e.g., by gravity), but the carriage 102 is generally not in contact with surfaces other than the pipe, such as the ground, for example, while it is in motion.

The carriage 102 may be propelled along the stationary pipe through a mechanism external to the carriage (e.g., a pulley system, etc.) and/or the carriage may be self-propelled. In one embodiment, the carriage 102 comprises a carriage drive mechanism 104 configured to propel the carriage 102 in an axial direction along a portion of the pipe. It will be appreciated that the term "axial" generally refers to a direction along the length of the pipe, the direction of fluid flow within the pipe and/or a plane parallel to either of these directions. Likewise, the term "transverse" refers to a direction that cuts across the axial direction. That is, "transverse" can be said to correspond to a plane perpendicular to the length of the pipe and/or to the direction of fluid flow along the length of the pipe.

A radiation source 108 and a radiation detector 110 may be operably coupled the carriage 102. The source 108 is configured to emit radiation in a pyramidal, wedge, fan, or other shaped beam. In a preferred embodiment, the emitted radiation is ionizing radiation. In one example, the radiation source 108 is a gamma ray source sized to provide an adequate number of gamma rays based upon characteristics of the pipe (e.g., its composition).

The amount of radiation emitted and/or the trajectory of the emitted radiation may be predetermined based upon the desired movement of the carriage 102, for example. In one example, the radiation source 108 emits a beam of radiation having an axial dimension greater than or equal two twice the diameter of the pipe being inspected to promote speed. An axial dimension greater than or equal two twice the diameter of the pipe may allow the carriage to move at a speed of about two inches per second to a speed of about 75 inches per second, for example. The source 108 may also be configured to emit radiation from a focal spot that is sized and/or shaped similar to an element or channel of the detector 110 (e.g., making mathematical modeling easier).

The radiation detector 110 may be situated in an axial plane that is on a diametrically opposing side of the pipe from the source 108 (e.g., the detector 110 is about 180° away from the source 108). In this way, the detector 110 may detect radiation, emitted from the source 108, after the radiation has traversed a wall of the pipe. It will be understood to those skilled in that art that the radiation detector 110 may be a direct conversion detector such as cadmium zinc telluride scintillator-based detector, or it may be an indirect conversion detector such as a $CdWO_4$ crystal detector or other scintillator-based detector, for example. It will also be understood to those skilled in the art that the detector 110 may be a multi-element detector configured to resolve a pyramidal shaped beam of radiation emitted from the radiation source 108 into many small sub-beams (e.g., to improve the quality of data generated based upon the detected radiation).

The detector 110 may be configured based upon the desired movement of the carriage 102 and/or the object being scanned. For example, to promote speed, the detector 110 may have an axial dimension that is at least two times greater than its transverse dimension. The detector 110 may also be configured to resolve a spatial resolution between about 0.5 and 1.0 times the wall thickness of the pipe being scanned. That is, the detector 110 may be configured to detect when the pipe's wall that has deteriorated to less than one-half of its original thickness in a particular area, for example.

The detector 110 may also be configured to counterbalance the weight of the radiation source 108. In one example, the radiation source 108, including a radiation shield, and the detector 110 are configured for transverse motion about the pipe (e.g., to rotate about the pipe), and the detector 110 comprises a counterweight so that the center of mass of the radiation source 108 and the detector 110 is substantially coincident with a center of the transverse motion (e.g., an axis of rotation).

The carriage drive mechanism 104, the radiation source 108, and/or the detector 110 may be operably coupled with a first data transceiver 112. The first data transceiver 112 may transceive (e.g., send and/or receive) data related to the carriage drive mechanism 104, the radiation source 108, and/or the detector 110 (collective referred to as the "devices"). In one embodiment, the first data transceiver 112 receives data from one or more devices and transmits it to a second data transceiver 114 located remotely (e.g., on a remote station one hundred yards from the pipe). The second data transceiver 114 may also transmit data to the first data transceiver 112, wherein the first data transceiver 112 sends the data to its designated device.

The apparatus 100 may also comprise a remote station 116 configured for monitoring one or more carriages. In one embodiment, the remote station 116 is part of a truck or other motor vehicle that is mobile relative to the carriage 102. By way of example only, and not limitation, the remote station 116 may be moved while the carriage is moving along the pipe so that a substantially consistent distance is maintained between the remote station 116 and the carriage 102 (e.g., one hundred yards there-between). The remote station 116 may comprise a computer having a graphical user interface 118 configured to display information related to the one or more carriages, such as their respective trajectories and/or display information related to other components comprised within the remote station 116. For example, the graphical user interface 118 may display a wall thickness of a portion of the pipe based upon calculations made by a data collection mechanism 120 and/or display whether radiation from the radiation source 108 is detected by a radiation measuring device 119 within the remote station 116 (e.g., to mitigate the possibility of radiation exposure to human inspectors near the remote station 116).

The remote station 116 may also comprise the data collection mechanism 120 and/or the second data transceiver 114. In one embodiment, the second data transceiver 114 receives data from the first data transceiver 112 and transmits it to the data collection mechanism 120. The data collection mechanism 120 may use the received data to determine one or more characteristics of the pipe, create a report based upon those determinations, and/or issue an alert if the determined characteristic(s) are outside a specified range. For example, when one or more determined characteristics are outside of a specified range, the data collection mechanism 120 may create a report that contains the measured value(s), the dimensions of an affected area(s), and the location of the affected area(s) along the pipe (e.g., so that a weak spot in the pipe may be repaired).

It will be appreciated that the second data transceiver 114 may also be configured to transceive data related to a controller 122. In one example, the controller 122 receives positional data from the carriage 102 and the controller 122 is configured to map the trajectory of the carriage 102 along the pipe. It will be appreciated that controller may also send commands to the carriage 102 (e.g., through the first and second data transceivers 112 and 114).

The second data transceiver 114 may also be configured to send data, such as reports containing information about troubled spots of the pipe, to a third data transceiver 124 attached to a central station 126 and/or receive data, such as maps depicting the pipe, from the third data transceiver 124. In one example, the third data transceiver 124 may also register a fault if the remote station 116 does not transmit to it within a given period of time so that emergency help may be dispatched. This may be particularly useful in Alaska, for example, where there is vast wilderness and extreme cold.

It will be appreciated that in some applications it may be more beneficial to not have a remote station 116 and/or a central station 126. In those applications some of the aforementioned devices, components, mechanisms, etc. may be situated differently. For example, the data collection mechanism 120 may be attached to the carriage 102 and/or the controller 122 may be located at the central station 126. Additionally, some of the aforementioned devices, components, mechanisms, etc. may have less applicability depending upon the circumstances.

Figure 2:
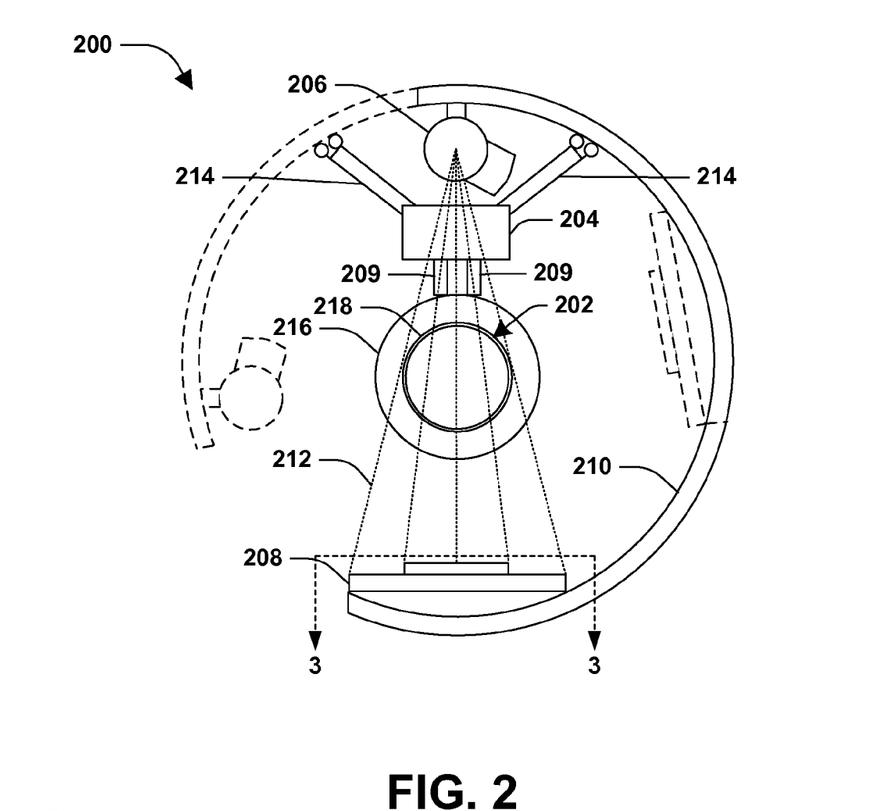
FIG. 2 illustrates an example apparatus for inspecting a pipe viewed from a transverse plane.

FIG. 2 illustrates a transverse plane of an example apparatus 200 configured to move axially along a stationary pipe 202 (e.g., going into and out of the page). The apparatus 200 comprises a carriage 204 (e.g., 102 in FIG. 1), a radiation source 206 (e.g., 108 in FIG. 1), and a detector 208 (e.g., 110 in FIG. 1). In the illustrated example, the carriage 204 moves axially along the pipe 202 by wheels 209 that couple the carriage to the pipe (e.g., the wheels 209 of the carriage 204 rest on top of the pipe 202).

In FIG. 2, the carriage 204 is operably coupled to the radiation source 206 and the detector 208 through a substantially arcuate, or rather c-shaped member 210. As illustrated by dotted lines, the c-shaped member may be configured to rotate about the pipe 202 in a generally transverse motion along guide rails 214, for example, physically attached to the carriage 204. That is, the c-shaped member 210 may rotate clockwise and/or counterclockwise about the pipe 202 through a plane substantially perpendicular to the direction of flow of fluid in the pipe 202 (into and/or out of the page). In this way, objects attached to the c-shaped member 210, such as the radiation source 206 and/or the detector 208, may rotate about the pipe 202 to inspect the pipe 202 from a plurality of angles or views.

It will be appreciated that in other embodiments, that the carriage 204 may not be coupled to the c-shaped member 210 and/or the detector 208 may not be rotated by the c-shaped member 210. In one example, the detector is directly attached to the carriage 204, and the carriage 204 is configured to rotate in a helical pattern through a plurality of axial and traverse planes relative to the pipe 202.

In some applications, the pipe 202 may comprise an insulation layer 216 configured to protect fluid traveling through the pipe from nature's elements. For example, pipes running through the Alaskan wilderness often comprise a layer of insulation to prevent fluid inside the pipe 202 from freezing. Generally in these applications, the pipe wall 218 has a thickness of between about 0.250 and about 0.500 inches, and the layer of insulation has a thickness of between about 2 and about 3 inches.

While the insulation layer 216 serves to protect fluid inside the pipe 202, it also hampers that ability to inspect the pipe 202. For example, as portions of the interior surface of the pipe wall 218 deteriorate and break away, the fluid carries the particles downstream. Therefore, more radiation will be detected in areas where the interior surface of the pipe wall 218 has a pit, divot, or other non-uniformity than in areas where little to no deterioration has occurred. However, portions of the exterior surface of the pipe wall 218 that deteriorate and would otherwise break away may be held in place by the insulation layer 216. Therefore, a substantially equal amount of radiation will be detected in an area where the exterior surface has significantly deteriorated and in an area where the exterior surface has experienced little to no deterioration, making detection of the exterior deterioration difficult.

Figure 3:
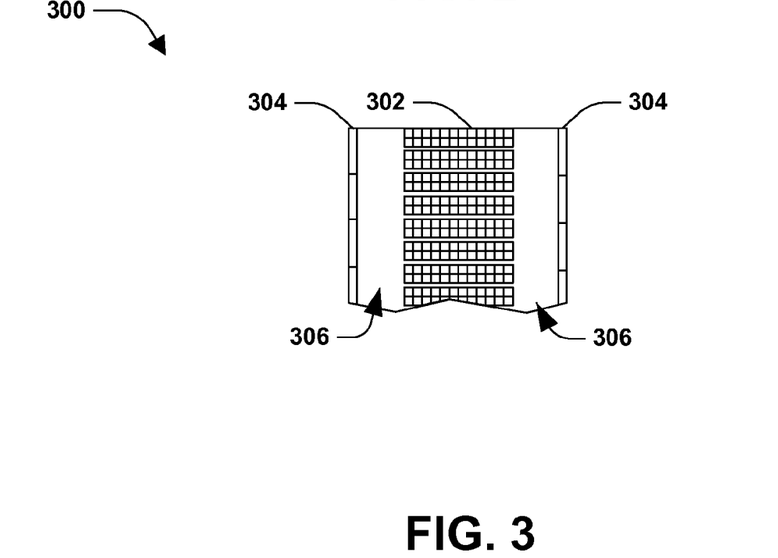
FIG. 3 illustrates an example detector array.

FIG. 3 illustrates one means of detecting deterioration on both the interior and exterior surfaces of a pipe wall (e.g., 218 in FIG. 2). More particularly, FIG. 3 illustrates an example detector 300 (e.g., 208 of FIG. 2 taken along phantom lines 3-3) of a pipe inspection apparatus (e.g., 100 in FIG. 1). The detector 300 comprises two detector arrays, a first array 302 and a second array 304. It will be understood to those skilled in that art that each array of the detector 300 may comprises a plurality of smaller detectors, or rather detector elements or channels (e.g., represented as small squares or rectangles), configured to detect small beams of radiation that have traversed the pipe (e.g., 202 in FIG. 2). The first array 302 may be configured to detect radiation indicative of the interior surface of the pipe wall. The second array 304, separated from the first array 302 by a gap 306, may be configured to detect radiation indicative of protrusions (e.g., external rust) on the exterior surface of the pipe wall. In the illustrated example, the second array 304 is narrower in the transverse dimension than the first array 302 in order to improve radial resolution (e.g., to detect non-uniformities that would otherwise be undetectable due to the presence of insulation that keeps outer surface rust, etc. in place). It will be appreciated that radiation indicative of the outer surface (e.g., detected by the second array 304) and radiation indicative of the inner surface (e.g., detected by the first array 302) may be combined or otherwise compared (e.g., by a data collection mechanism similar to 120 in FIG. 1) to determine characteristics of the wall (e.g., how thick the wall is at a given point along the pipe).

Returning to FIG. 2, occasionally, the pipe 202 may be supported by a pipe support. For example, hydrocarbon, or oil, pipes are commonly supported on a plurality of pipe supports. In this way, the pipes are located above and substantially parallel to the ground. To provide a more complete inspection of the pipe 202, the radiation detector 208 is configured to detect radiation 212 that has traversed both a pipe support and the pipe wall 218 (e.g., supported by the pipe support). That is, as the carriage 204 moves along the pipe 202 and encounters a pipe support, the detector 208 is configured to detect radiation 212 that has passed through a pipe support as well as a portion of the pipe wall 218 adjacent to, or in close proximity to (e.g., touching/supported by) the pipe support. For example, the detector 208 may be positioned substantially beneath the pipe 202 and may be configured to pass beneath a portion of the pipe support. It will be appreciated that the term "portion" is used herein in a broad sense and intended to include any and all of the object the term "portion" is being used to describe (e.g., the detector may be configured to pass beneath the entire pipe support or just some or a part of the pipe support).

Figure 4:
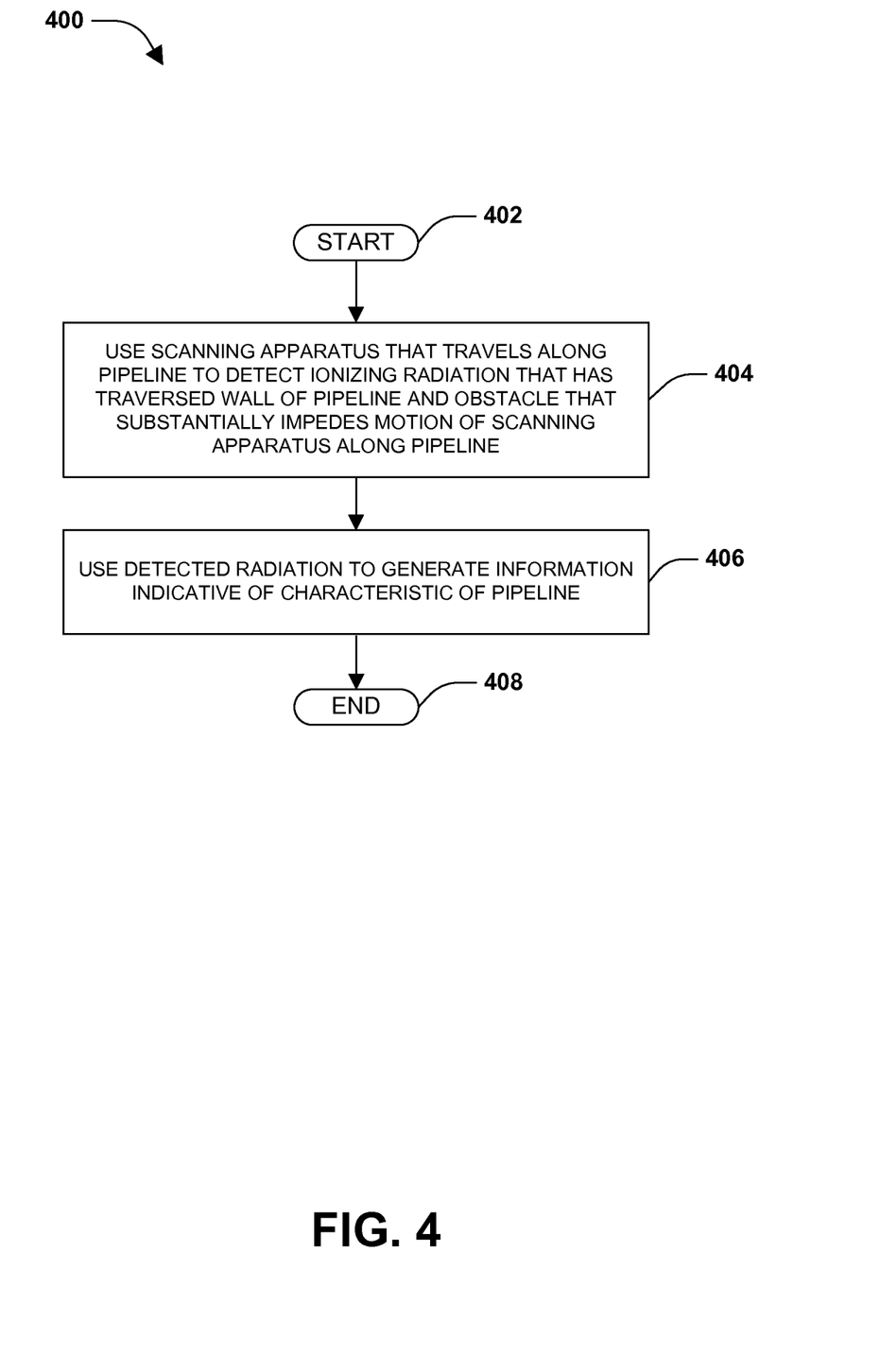
FIG. 4 illustrates an example method for generating information indicative of a characteristic of a pipe.

FIG. 4 illustrates a method 400 for generating information indicative of a characteristic of a pipe. While the method 400 is illustrated and described below as a series of acts or events, the present disclosure is not limited by the illustrated ordering of such acts or events. For example, some acts may occur in different orders and/or concurrently with other acts or events apart from those illustrated and/or described herein. In addition, not all illustrated acts may be required. Further, one or more of the acts depicted herein may be carried out in one or more separate acts or phases.

The method 400 starts at 402, and a scanning apparatus that travels axially along a pipe, or rather a pipeline, is used to detect ionizing radiation that has traversed a wall of the pipe and an obstacle, such as a pipe support, that substantially impedes the motion of the scanning apparatus along the pipe at 404.

At 406, the detected radiation is used to generate information indicative of a characteristic of the pipe, such as a thickness of a wall of the pipe, for example. The method ends at 408.

To illustrate a specific example of how FIG. 4's method could be implemented, FIG. 4 is discussed with reference to a series of system diagrams in FIGS. 5-18.

Figure 5:
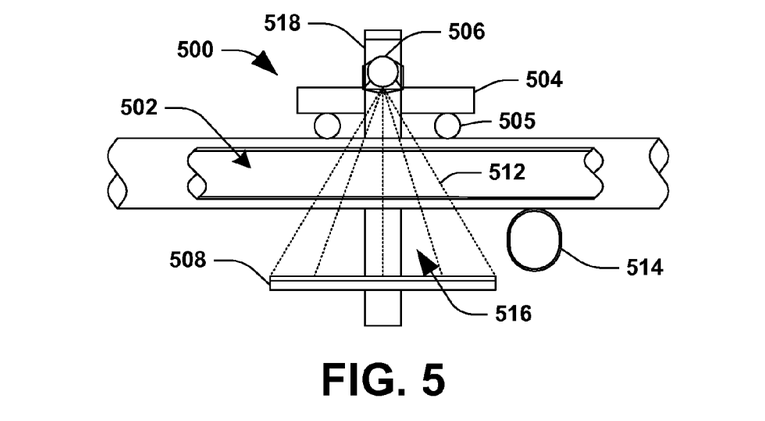
FIG. 5 illustrates an example apparatus, viewed from an axial plane, that is moving along a portion of a pipe and encountering an obstacle.
Figure 6:
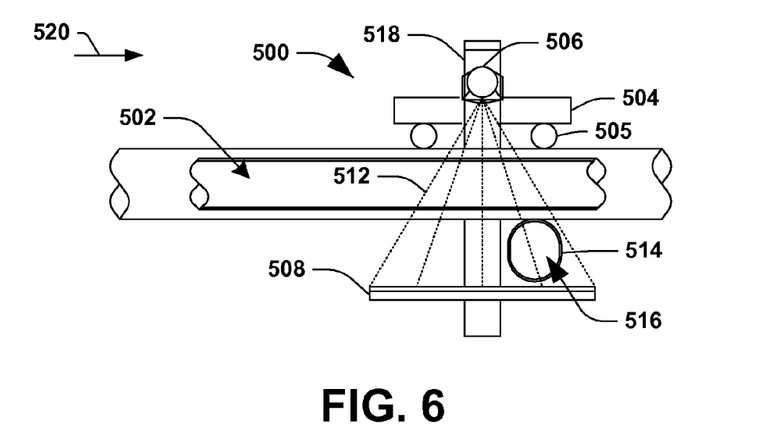
FIG. 6 illustrates an example apparatus, viewed from an axial plane, that is moving along a portion of a pipe and encountering an obstacle.
Figure 7:
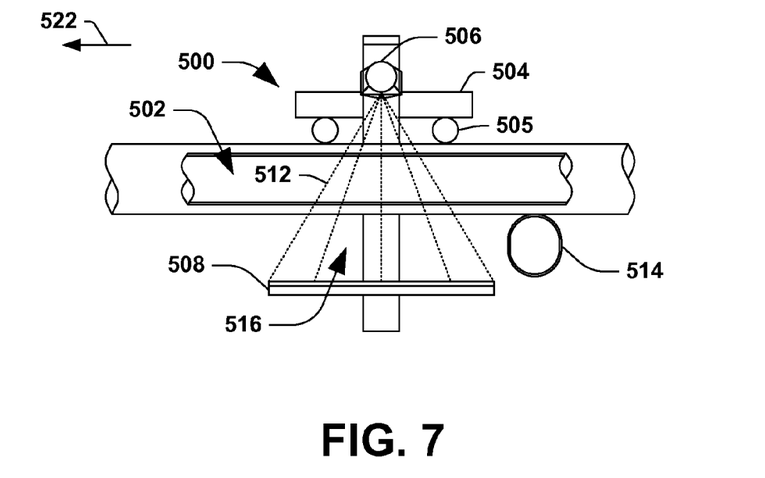
FIG. 7 illustrates an example apparatus, viewed from an axial plane, that is moving along a portion of a pipe and encountering an obstacle.

FIGS. 5-7 illustrate an example apparatus 500 (e.g., 200 in FIG. 2) as it moves axially along a stationary pipe 502 (e.g., 202 in FIG. 2). More particularly, FIG. 5 shows a carriage 504 (e.g., 204 in FIG. 2) travelling/moving (e.g., via wheels 505) axially along a pipe 502 and approaching a pipe support 514 or other obstacle. Operably coupled to the carriage 504 are a radiation source 506 (e.g., 206 in FIG. 2) and a radiation detector 508 (e.g., 208 in FIG. 2). In the illustrated example, the source 506 and detector 508 are physically coupled to the carriage 504 through a c-shaped member 518 (e.g., 210 in FIG. 2). Radiation 512 (e.g., 212 in FIG. 2) that traverses the pipe 502 is detected by the radiation detector 508 situated on a substantially diametrically opposing side of the pipe 502 from the radiation source 506.

The support 514 is generally transverse to the pipe 502 (e.g., the support 514 is going into and out of the page) and the apparatus 500 is configured to allow a portion of the support 514 to fit between the apparatus 500 and the pipe 502. In the illustrated example, the apparatus 500 comprises a substantially material free region 516 that allows a portion of the apparatus 500 to be positioned with respect to the support 514 to detect radiation 512 from the source 506 that has traversed both the support 514 and the pipe 502. In FIG. 5, the substantially material free region 516 is a region between the detector 508 and the pipe 502, wherein the detector 508 is spaced away from the pipe 502 a distance that allows the support 514 to fit between the pipe 502 and the detector 508. It will be understood to those skilled in the art the other configurations for creating a substantially material free region 516 are also contemplated. In one example, the substantially material free region 516 is a region between the source 506 and the pipe 502 (e.g., the locations of the source 506 and the detector 508 are reversed).

FIG. 6 illustrates the example apparatus 500 encountering, or rather in close proximity to the pipe support 514 while the carriage 504 is moving axially to the right 520. In the illustrated example, the support 514 is located beneath and substantially adjacent to the pipe 502. The apparatus 500 is configured so that the detector 508 passes beneath a portion of the support 514 during a time when the detector 508 detects radiation from the source 506. That is, the apparatus 500 is positioned in such a way that a portion of the support 514 or other obstacle is in the substantially material free region 516 of the apparatus 500. While the support 514 is in the substantially material free region 516, the source 506 may emit radiation 512 that traverses a wall of the pipe 502 and a portion of the support 514, and is then detected by the detector 508.

It will be understood to those skilled in the art that there are numerous ways of creating a substantially material free region such as that illustrated in FIGS. 5-7. In the illustrated example, the detector 508 has a wider axial dimension than the axial dimension of the c-shaped member 518. In this way, the detector 508 can slide, or rather be position beneath the support 514, even while the c-shaped member 518 abuts or is blocked by the support 514. In another example, the detector 508 is offset from a c-shaped member 518 or other bracket supporting the detector 508, thus allowing the detector 508 to be positioned under the support 514 regardless of whether the axial movement of the c-shaped member is impeded by the support 514.

FIG. 7 illustrates the example apparatus 500 after radiation 512 that has traversed a wall of the pipe 502 and the pipe support 514 has been detected. In the illustrated example, the apparatus 500 has reversed direction (e.g., now moving axially to the left 522) after detecting radiation 512 that traversed both the pipe 502 and the pipe support 514. It will be understood to those skilled in that art that by repeatedly moving in a first direction (e.g., to the right 520 as illustrated in FIG. 6) and then altering, or rather reversing direction (e.g., by moving to the left 522 as illustrated in FIG. 7), the detector 508 may make a plurality of passes along a length of the pipe 502 during a time when the detector 508 is detecting radiation 512 from the source 506. In this way, the detector 508 may take multiple readings along a particular length of the pipe 502.

Figure 8:
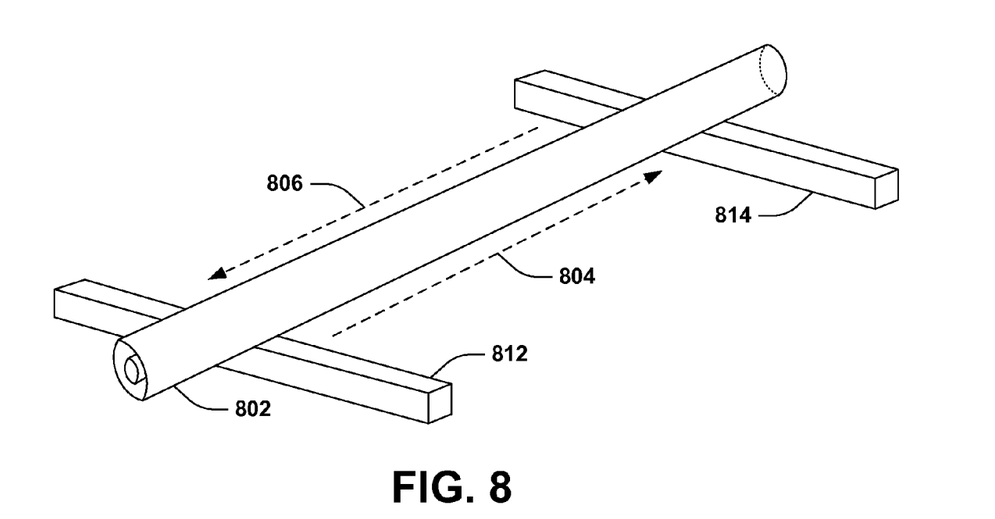
FIG. 8 illustrates a pipe supported by a first and second pipe support.

As illustrated in FIG. 8, the pipe may be supported by first and second axially-spaced pipe supports 812 and 814 (e.g., 514 in FIG. 5). A scanning apparatus (e.g., 500 in FIG. 7) may be configured to scan the pipe 802 (e.g., 502 in FIG. 7) at the first and second supports 812 and 814 and therebetween. That is, a carriage (e.g., 504 in FIG. 7) may be configured for movement between the first and second supports 812 and 814 and a radiation source (e.g., 506 in FIG. 7) may be configured to emit radiation (e.g., 512 in FIG. 7) substantially continuously during movement. In this way, the length of pipe 802 between the first and second supports 812 and 814, and the portions of the pipe 802 supported on the first and second supports 812 and 814 may be inspected. In one embodiment, the apparatus scans the length of pipe 802 between the first and second supports 812, 814 in a first direction 804 and then scans the same length of pipe in a second direction 806 (e.g., in a back and forth motion).

With reference back to FIG. 2, it will be appreciated that the detector 208 and/or the radiation source 206 may be configured to rotate in a transverse motion (e.g., around the pipe) as the apparatus 200 moves axially along the length of the pipe 202 (e.g., as illustrated in FIG. 8) to detect data indicative of a plurality of views of the pipe 202. In one example, the detector 208 rotates in a helical or spiral-like manner as the apparatus 200 moves along the pipe 202. In another example, the detector 208 is fixed at a first transverse angle (e.g., relative to the pipe) as the apparatus 200 moves in a first direction (e.g., 804 in FIG. 8) and is fixed at a second transverse angle as the apparatus 200 moves in a second direction (e.g., 806 in FIG. 8). That is, the detector 208 is scanned back and forth, but at different transverse angles for respective scans (e.g., thereby tracking a zig-zag pattern).

FIGS. 9-18 illustrate movement of an example scanning apparatus (e.g., 500 in FIG. 5) to scan a length of pipe including at first and second axially-spaced pipe supports 812 and 814. It will be appreciated that a detector 808 of the apparatus moves through a plurality of transverse angles as the pipe is scanned. It will also be understood that this movement allows radiation indicative of the pipe 802 to be obtained from a plurality of different views, which promotes accurate measurements. In one embodiment, the radiation, indicative of the pipe 802 from a plurality of angles, may be combined using computed tomography techniques known to those skilled in the art to create images of the pipe 802 being scanned. However in some applications, such as when the apparatus is measuring wall thickness, for example, an image may not be produced (e.g., because it is not necessary for determining the characteristic being measured). It will also be appreciated that some transverse angles illustrated in FIGS. 9-18 may not be suited for instances in which the detector 808 is in close proximity to the supports because the detector 808, for example, may make physical contact with the obstacle (e.g., preventing the apparatus from continuing its scan). That is, at some transverse angles the detector 808 may be unable to be positioned about the obstacle to detect radiation that has traversed both a wall of the pipe 802 and the obstacle (e.g., a pipe support) and/or positioned such that the detector's movement is otherwise unimpeded by the obstacle.

Figure 9:
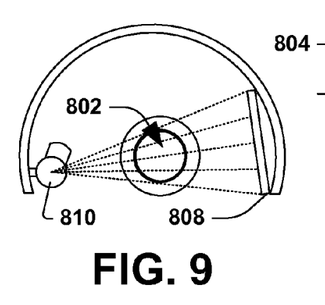
FIG. 9 illustrates a detector located at a first transverse angle with respect to a pipe.
Figure 10:
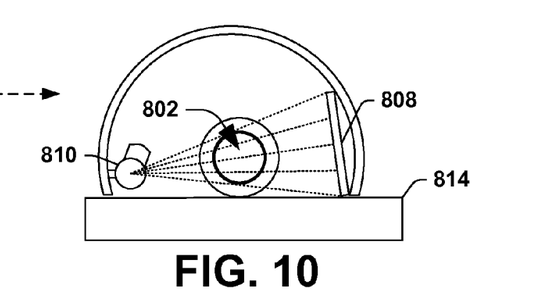
FIG. 10 illustrates a detector near an obstacle and located at a first transverse angle with respect to a pipe.

As illustrated in FIG. 9, while moving in a first direction 804 (e.g., away from support 812 and toward support 814) the detector 808 may be located at a first transverse angle (e.g., with respect to the pipe). When the detector 808 reaches the second support 814, the detector 808 may continue moving in the first direction 804, with the detector 808 located at the first transverse angle, as illustrated in FIG. 10. This arrangement effectively allows the scanning apparatus to pass over the second support 814.

Figure 11:
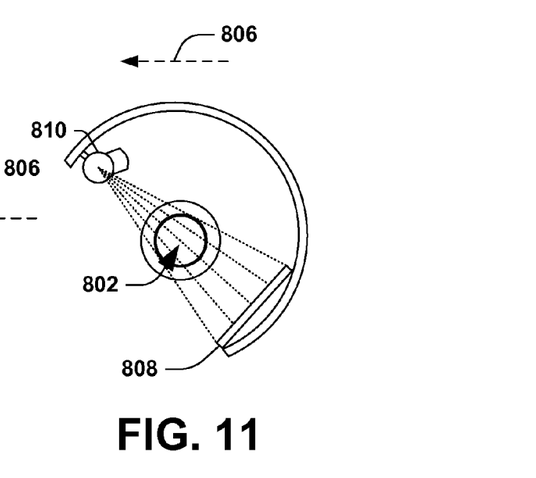
FIG. 11 illustrates a detector located at a second transverse angle with respect to a pipe.

Once the detector 808 has detected radiation that has traversed a portion of the pipe 802 in close proximity to the second support 814 (e.g., a portion of the pipe 802 on top of the second support 814), the detector 808 may reverse direction and start moving in a second direction 806. Once the detector 808 has moved far enough along in the second direction 806 such that it has cleared or is no longer over top of the second support 814 (recall that the detector 808 has a somewhat substantial axial length into and/or out of the page), the detector's position may be changed, or rather rotated (e.g., 72 degrees from the first transverse angle), to a second transverse angle (e.g., without bumping into the second support 814), as illustrated in FIG. 11. It will be appreciated that motion in the axial direction may be halted while transverse movement occurs as provided herein.

Figure 12:
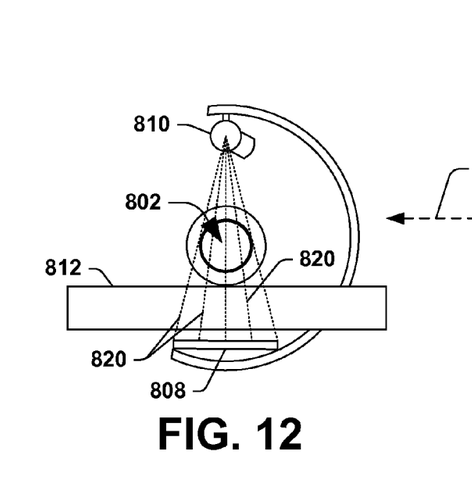
FIG. 12 illustrates a detector near an obstacle and located at a third transverse angle with respect to a pipe.

After being rotated to the second transverse angle, the detector 808 may continue moving along the pipe in the second direction 806 until it reaches the first support 812. When the detector 808 reaches the first support 812, the detector 808 may be (halted and then) rotated again (e.g., 90 degrees from the first transverse angle) to a third transverse angle so that the first support 812 does not impede the detector from continuing movement in the second direction 806 (e.g., so that the detector 808 does not bump into the first support 812), as illustrated in FIG. 12.

Figure 13:
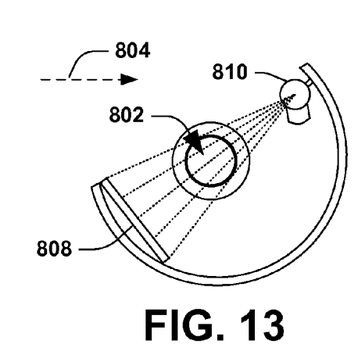
FIG. 13 illustrates a detector located at a fourth transverse angle with respect to a pipe.

After being rotated through to the third transverse angle, the detector 808 may then continue moving in the second direction 806 so that a portion of the first support 812 is situated between the detector 808 and the pipe 802 (e.g., a portion of the detector 808 is under the first support 812). This allows radiation 820 that has traversed both the support 812 and the pipe 802 to be detected by the detector 808. The detector 808 may then reverse direction and start moving in the first direction 804. When the detector 808 has cleared the first support 812 (e.g., is no longer under the first support 812), the detector 808 may be rotated (e.g., 144 degrees from the first transverse angle) to a fourth transverse angle, as illustrated in FIG. 13, and may continue moving in the first direction 804 until it reaches the second support 814. It will be appreciated that the supports 812, 814 are not illustrated in FIGS. 9, 11, 13, 15 and 17 since the detector 808 is not in as close proximity to the supports 812 or 814 as compared to the orientations illustrated in FIGS. 10, 12, 14, 16 and 18 where the detector 808 has "reached" the supports 812 or 814.

Figure 14:
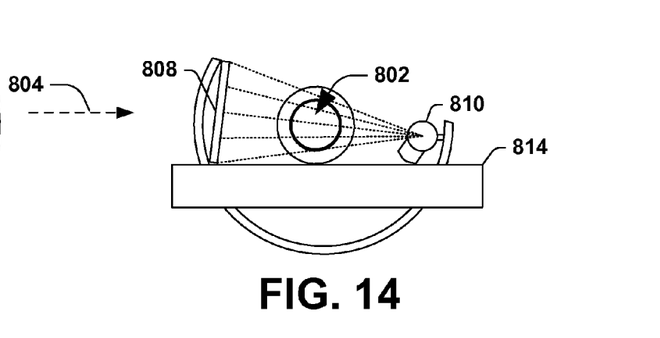
FIG. 14 illustrates a detector near an obstacle and located at a fifth transverse angle with respect to a pipe.

When the detector 808 reaches the second support 814, the detector 808 may be rotated again (e.g., 180 degrees from the first transverse angle) to a fifth transverse angle that does not impede the detector 808 from continuing movement in the first direction 804, as illustrated in FIG. 14. The detector 808 may then continue moving in the first direction 804 to detect radiation that has traversed a portion of the pipe 802 in close proximity to the second support 814. Note, however, that unlike the orientation illustrated in FIG. 10, a c-shaped member of the apparatus (e.g., which supports the detector 808 and a radiation source 810) is impeded by the second support 814. However, the (elongated) shape of the detector 808 (e.g., into and out of the page) still allows the portion of the pipe 802 directly above the second support 814 to be scanned. Accordingly, at this juncture, in the example illustrated, the portion of the pipe 802 resting upon the second support 814 has been scanned at two different transverse angles that happen to be 180° apart. That is, the orientation of the source 810 and the detector 808 is reversed in FIGS. 10 and 14. These different "views" contribute to better insight or fidelity into the wear of the pipe 802 (e.g., coupled with additional data or information about the pipe).

Figure 15:
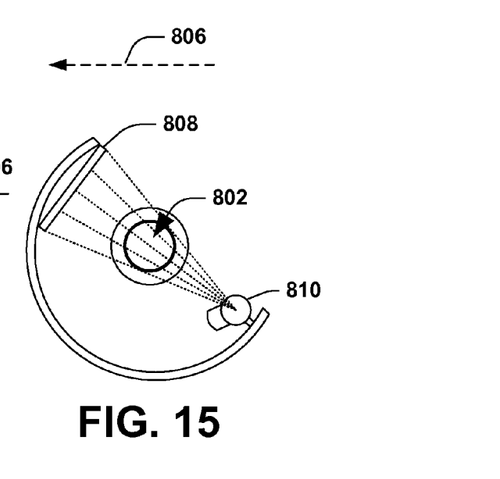
FIG. 15 illustrates a detector located at a sixth transverse angle with respect to a pipe.
Figure 16:
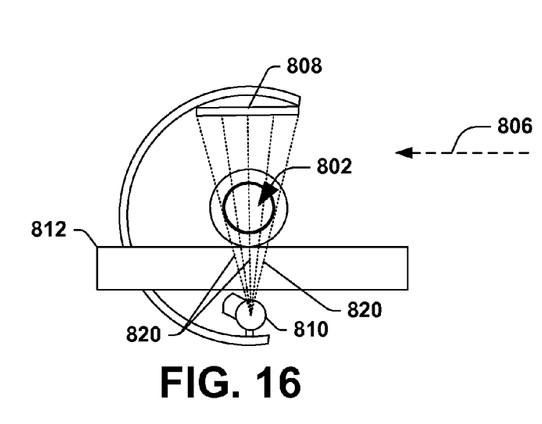
FIG. 16 illustrates a detector near an obstacle and located at a seventh transverse angle with respect to a pipe.

The detector 808 may then reverse direction and start moving in the second direction 806. When the detector 808 has cleared the second support 814, the detector 808 may be rotated (e.g., 216 degrees from the first transverse angle) to a sixth transverse angle, as illustrated in FIG. 15, and may continue moving in the second direction 806 until it reaches the first support 812. When the detector 808 reaches the first support 812, the detector 808 may be rotated again (e.g., 270 degrees from the first transverse angle) to a seventh transverse angle that does not impeded the detector from continuing movement in the second direction 806, as illustrated in FIG. 16. The detector 808 may then continue moving in the second direction 806 to detect radiation that has traversed a portion of the pipe 802 in close proximity to the first support 812. In the illustrated example, the first support 812 is situated between the source 810 and the pipe 802 (e.g., the source 810 is under the first support 812). This allows radiation 820 that has traversed both the support 812 and the pipe 802 to be detected by the detector 808. Similar to the preceding discussion regarding FIGS. 10 and 14, in this example, the portion of the pipe 802 resting upon the first support 812 has now been "viewed" from two different angles that happen to be 180° apart, once in FIG. 12 and again in FIG. 16.

Figure 17:
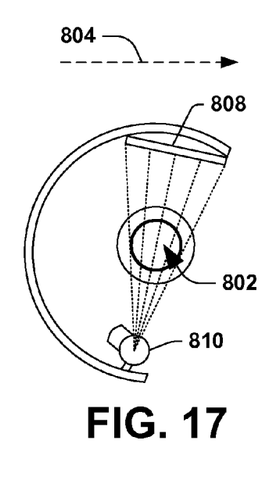
FIG. 17 illustrates a detector located at an eighth transverse angle with respect to a pipe.
Figure 18:
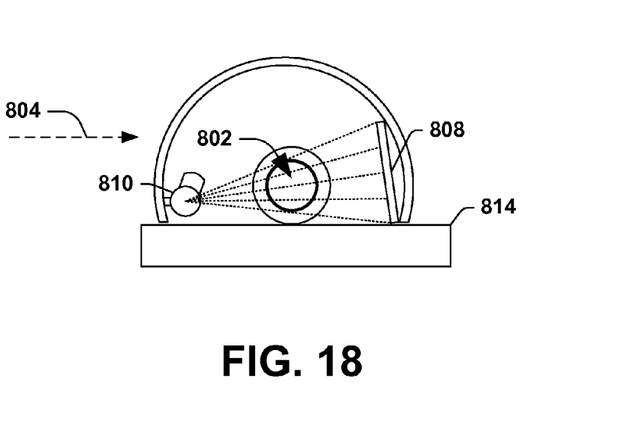
FIG. 18 illustrates a detector near an obstacle and located at a first transverse angle with respect to a pipe.

The detector 808 may then reverse direction and move in the first direction 804. When the detector 808 has cleared the first support 812, the detector 808 may be rotated (e.g., 288 degrees from the first transverse angle) to an eighth transverse angle, as illustrated in FIG. 17, and may continue moving in the first direction 804 until it reaches the second support 814 (thus acquiring yet another "view" of the pipe 802 at locations between the first 812 and second 814 supports). When the detector 808 reaches the second support 814, the detector 808 may be rotated again to the first transverse angle, as illustrated in FIG. 18 (which is also the original orientation illustrated in FIG. 10). That is, this section of pipe, including at first and second support 812, 814 locations, may be sufficiently scanned such that the apparatus is reset to its original orientation. The detector 808 may then move to another section of the pipe 802 positioned between the second support 814 and a third support, and repeat the acts herein described between the second support 814 and the third support.

It will be appreciated that while FIGS. 9-18 illustrate the detector 808 rotating substantially 360° about a pipe 802, the detector 808 and/or another portion of the apparatus, such as the radiation source 810, may be configured to rotate less than or equal to 360° about the pipe 802. In one example, the total range of traverse angles through which the detector 808 is varied does not exceed about 180° (e.g., the detector 808 never rotates about the entire circumference of the pipe 802). In another example, the total range of rotation the detector 808 makes is substantially beneath the pipe 802 (e.g., the detector 808 may never rotate to the side and/or above or over top of the pipe 802). Merely scanning the bottom of the pipe may be sufficient in some instances because that is where the majority of wear and tear occurs, given that fluid flow primarily occurs in the bottom or lower part of the pipe. Nevertheless, the particular transverse angles and movements described herein are merely examples, and the apparatus can move in any desired manner to acquire radiation and generate information therefrom indicative of a characteristic of the pipeline, including at locations where the pipeline is adjacent to, in contact with and/or otherwise supported by cross-braces or other types of pipe supporting structures, without having to be removed from the pipe.

What is claimed is:

1. A pipe inspection apparatus comprising:
a carriage configured to be mounted to a pipe and configured for movement along the pipe, the carriage comprising:
a substantially c-shaped member configured for rotation relative to the pipe about an axis of rotation extending in a direction parallel to an axial direction of the pipe;
an ionizing radiation source coupled to the c-shaped member; and
a radiation detector coupled to the c-shaped member and positioned substantially diametrically opposite the ionizing radiation source relative to the pipe, the radiation detector extending beyond the c-shaped member in the axial direction to facilitate positioning a support beam to which the pipe is mounted between a portion of the radiation detector and the pipe and to facilitate an examination of a portion of the pipe in contact with the support beam, the support beam extending in a direction substantially transverse to the axial direction of the pipe.

2. The apparatus of claim 1, a mass of the carriage supported by the pipe.

3. The apparatus of claim 1, the carriage mounted to the pipe via tracks that are at least one of physically coupled to the pipe or embedded in the pipe.

4. The apparatus of claim 1, a center of mass of the c-shaped member located proximate the axis of rotation.

5. The apparatus of claim 1, the carriage comprising a radiation shield configured to shield the ionizing radiation source.

6. The apparatus of claim 1, the radiation detector comprising at least a first detector array and a second detector array, the first detector array having a transverse dimension that is greater than a transverse dimension of the second detector array.

7. The apparatus of claim 1, an axial dimension of the radiation detector at least two times a diameter of the pipe.

8. The apparatus of claim 1, the pipe configured to transport one or more hydrocarbons.

9. The apparatus of claim 1, wherein:
the c-shaped member is configured to rotate to a first position relative to the support beam to facilitate the examination of the portion of the pipe in contact with the support beam, and
the c-shaped member is configured to rotate to a second position relative to the support beam to facilitate traversing the support beam, the first position different than the second position.

10. The apparatus of claim 1, the ionizing radiation source comprising an x-ray source.

11. A pipe inspection apparatus comprising:
a carriage configured for movement along a pipe, the carriage comprising:
- a substantially c-shaped member configured for rotation relative to the pipe about an axis of rotation extending in a direction parallel to an axial direction of the pipe;
- an ionizing radiation source coupled to the c-shaped member; and
- a radiation detector coupled to the c-shaped member and positioned substantially diametrically opposite the ionizing radiation source relative to the pipe, the radiation detector extending beyond the c-shaped member in the axial direction to facilitate positioning a support beam to which the pipe is mounted between a portion of the radiation detector and the pipe and to facilitate an examination of a portion of the pipe in contact with the support beam, the support beam extending in a direction substantially transverse to the axial direction of the pipe, and wherein:
    - the c-shaped member is configured to rotate to a first position relative to the support beam to facilitate the examination of the portion of the pipe in contact with the support beam, and
    - the c-shaped member is configured to rotate to a second position relative to the support beam to facilitate traversing the portion of the pipe in contact with the support beam.

12. The apparatus of claim 11, the axis of rotation located proximate a center of the pipe from which a radius of the pipe is measured.

13. The apparatus of claim 11, a center of mass of the c-shaped member located proximate the axis of rotation.

14. The apparatus of claim 11, the radiation detector comprising at least a first detector array and a second detector array, the first detector array having a transverse dimension that is greater than a transverse dimension of the second detector array.

15. The apparatus of claim 11, the second position spaced apart from the first position by about 90 degrees.

16. The apparatus of claim 11, the radiation detector having a first axial dimension and the c-shaped member having a second axial dimension, the first axial dimension greater than the second axial dimension.

17. The apparatus of claim 11, the second position providing for movement of the radiation detector in the axial direction from a first position spatially proximate a first radial surface of the support beam to a second position spatially proximate a second radial surface of the support beam that is substantially diametrically opposite the first radial surface of the support beam, the first radial surface laying in a first plane substantially parallel to a radius of the pipe and the second radial surface laying in a second plane substantially parallel to the first plane.

18. A method for inspecting a pipe via ionizing radiation, comprising:
- while mounted to the pipe, performing a helical scan of the pipe by rotating an ionizing radiation source and a radiation detector about an axis of rotation extending in a direction parallel to an axial direction of the pipe and moving a carriage supporting the ionizing radiation source and the radiation detector in a first direction parallel to the axial direction; and
- upon encountering a support beam extending in a direction transverse to the axial direction, halting the rotating and the moving and positioning the radiation detector in a first position relative to the support beam such that the support beam is between the pipe and a portion of the radiation detector to facilitate an examination of a portion of the pipe in contact with the support beam.

19. The method of claim 18, comprising:
- after the examination of the portion of the pipe in contact with the support beam, moving the carriage in a second direction opposite the first direction to facilitate a rotation of the radiation detector relative to the pipe such that the radiation detector does not encounter the support beam; and
- positioning the radiation detector in a second position relative to the support beam to facilitate traversing the portion of the pipe in contact with the support beam.

20. The method of claim 19, upon traversing the portion of the pipe in contact with the support beam, resuming the helical scan.

* * * * *